US010096104B2

(12) United States Patent
Choi et al.

(10) Patent No.: US 10,096,104 B2
(45) Date of Patent: Oct. 9, 2018

(54) SYSTEMS AND METHODS FOR PREDICTING LOCATION, ONSET, AND/OR CHANGE OF CORONARY LESIONS

(71) Applicant: HeartFlow, Inc., Redwood City, CA (US)

(72) Inventors: Gilwoo Choi, Mountain View, CA (US); Leo Grady, Millbrae, CA (US); Charles A. Taylor, Menlo Park, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 15/186,962

(22) Filed: Jun. 20, 2016

(65) Prior Publication Data

US 2016/0300350 A1    Oct. 13, 2016

Related U.S. Application Data

(63) Continuation of application No. 14/011,151, filed on Aug. 27, 2013, now Pat. No. 9,805,463.

(51) Int. Cl.

| | |
|---|---|
| *G06F 19/10* | (2011.01) |
| *A61B 5/02* | (2006.01) |
| *G06T 7/00* | (2017.01) |
| *A61B 5/00* | (2006.01) |
| *G06N 99/00* | (2010.01) |
| *G06K 9/46* | (2006.01) |
| *G06K 9/66* | (2006.01) |
| *G06N 7/00* | (2006.01) |
| *G16H 50/50* | (2018.01) |
| *G16H 50/20* | (2018.01) |

(52) U.S. Cl.
CPC ........ *G06T 7/0012* (2013.01); *A61B 5/02007* (2013.01); *A61B 5/7275* (2013.01); *G06K 9/4604* (2013.01); *G06K 9/66* (2013.01); *G06N 7/005* (2013.01); *G06N 99/005* (2013.01); *G16H 50/20* (2018.01); *G16H 50/50* (2018.01); *G06T 2207/10081* (2013.01); *G06T 2207/10088* (2013.01); *G06T 2207/10104* (2013.01); *G06T 2207/10108* (2013.01); *G06T 2207/10132* (2013.01); *G06T 2207/30096* (2013.01); *G06T 2207/30101* (2013.01); *G06T 2207/30104* (2013.01)

(58) Field of Classification Search
None
See application file for complete search history.

(56) References Cited

U.S. PATENT DOCUMENTS

| | | | |
|---|---|---|---|
| 7,751,984 B2 | 7/2010 | Tang | |
| 8,315,812 B2 * | 11/2012 | Taylor | ................ A61B 5/02007 |
| | | | 382/128 |
| 2006/0171585 A1 | 8/2006 | Rinck | |
| 2010/0278405 A1 | 11/2010 | Kakadiaris et al. | |
| 2011/0060576 A1 | 3/2011 | Sharma et al. | |
| 2012/0041739 A1 | 2/2012 | Taylor | |
| 2012/0053918 A1 | 3/2012 | Taylor | |
| 2013/0094749 A1 | 4/2013 | Oh | |
| 2014/0073976 A1 | 3/2014 | Fonte et al. | |
| 2015/0066818 A1 | 3/2015 | Choi et al. | |

FOREIGN PATENT DOCUMENTS

| | | |
|---|---|---|
| CN | 101799864 | 1/2010 |
| EP | 2987105 | 3/2016 |
| JP | 2007-502676 | 2/2007 |
| JP | 2008-289861 | 3/2007 |
| JP | 2008-126077 | 6/2008 |
| JP | 2010-246776 | 11/2010 |
| JP | 20011-072500 | 4/2011 |
| JP | 2011-161104 | 8/2011 |
| JP | 2011-212156 | 10/2011 |
| JP | 2012-085721 | 5/2012 |

(Continued)

OTHER PUBLICATIONS

Sethian, J.A., "Fast Marching Methods and Level Set Methods for Propagating Interfaces", von Karman Institute Lecture Series, Computational Fluid Mechanics, 1998, pp. 1-60, Department of Mathematics University of California, Berkeley, California, USA.

Angelini, Elsa et al., 2005. "State-of-the-art of level Set Methods in Segmentation and Registration of Medical Imaging Modalities", Handbook of Biomedical Image Analysis—Registration Models. Kluwer Academic/ Plenum Publishers, 2005, pp. 47-102, Columbia University, New York, NY, USA.

Behrens, Thorsten et al., 2001. "Segmentation of Tubular Structures in 3D Images Using a Combination of The Hough Transform and a Kalman Filter", Proc. DAGM-Symp. Pattern Recognit., 2001, vol. 2191, pp. 406-413, International University in Germany.

(Continued)

*Primary Examiner* — Lori A. Clow
(74) *Attorney, Agent, or Firm* — Bookoff McAndrews, PLLC

(57) ABSTRACT

Systems and methods are disclosed for predicting the location, onset, or change of coronary lesions from factors like vessel geometry, physiology, and hemodynamics. One method includes: acquiring, for each of a plurality of individuals, a geometric model, blood flow characteristics, and plaque information for part of the individual's vascular system; training a machine learning algorithm based on the geometric models and blood flow characteristics for each of the plurality of individuals, and features predictive of the presence of plaque within the geometric models and blood flow characteristics of the plurality of individuals; acquiring, for a patient, a geometric model and blood flow characteristics for part of the patient's vascular system; and executing the machine learning algorithm on the patient's geometric model and blood flow characteristics to determine, based on the predictive features, plaque information of the patient for at least one point in the patient's geometric model.

17 Claims, 8 Drawing Sheets

(56) References Cited

FOREIGN PATENT DOCUMENTS

| WO | WO 2007/058997 | 5/2007 |
|----|----------------|--------|
| WO | WO 2013/071219 | 5/2013 |
| WO | WO 2015/030998 | 3/2016 |

OTHER PUBLICATIONS

Benmansour, Fethallah et al., "A New Interactive Method for Coronary Arteries Segmentation Based on Tubular Anisotropy", Proc. IEEE Int. Symp. Biomed. Imaging, 2009, pp. 41-44, Paris, France.

Fridman, Yonatan et al., "Segmenting 3D Branching Tubular Structures Using Cores", Proc. Med. Image Comput. Assist. Interv., 2003, pp. 570-577, Medical Image Display & Analysis Group University of North Carolina, Chapel Hill, NC, USA.

Yang, Yan et al., "Knowledge-Based 3D Segmentation and Reconstruction of Coronary Arteries Using CT Images", Proc. IEEE Eng. Med. Biol. Soc., 2004, pp. 1664-1666, Georgia Tech and Emory University, Atlanta, GA.

Yi, Jaeyoun et al., "A Locally Adaptive Region Growing Algorithm for Vascular Segmentation", Int. J. Imaging Syst. Technol., 2003 Wiley Periodicals, Inc., vol. 13, pp. 208-214, Department of Electrical Engineering and Computer Science, Korea Advanced Institute of Science and Technology.

Quek, Francis K.H. et al., "Vessel Extraction in Medical Images by Wave Propagation and Traceback", Vision Interfaces and Systems Laboratory (VISLab), Oct. 2000, pp. 1-37, Department of Computer Science and Engineering, Wright State University, Dayton, Ohio, USA.

Lesage, David et al., 2009. "A review of 3D vessel lumen segmentation techniques: Models, Features and extraction schemes", Medical Image Analysis 13, 2009, pp. 819-845, Siemens Corporate Research, Imaging and Visualization Dept., Princeton, NJ, USA.

Kim, H.J. et al., "Patient-Specific Modeling of Blood Flow and Pressure in Human Coronary Arteries", Annals of Biomedical Engineering, vol. 38, No. 10, Oct. 2010, pp. 3195-3209, Aeospace Engineering Sciences, University of Colorado at Boulder, Boulder, CO., USA et al.

Taylor, Charles A. et al., "Finite element modeling of blood flow: Relevance to artherosclerosis", 1998, (41 pages), Department of Surgery and Mechanical Engineering, Stanford University, Stanford, CA, U.S.A.

Les, Andrea S. et al., "Quantification of Hemodynamics in Abdominal Aortic Aneurysms During Rest and Exercise Using Magnetic Resonance Imaging and Computational Fluid Dynamics", Annals of Biomedical Engineering, Apr. 2010, vol. 38, No. 4, pp. 1288-1313, Department of Bioengineering, Stanford University, Stanford, CA, USA et al.

Shadden, Shawn C. et al., "Characterization of Coherent Structures in the Cardiovascular System", Annals of Biomedical Engineering, Jul. 2008, vol. 36, No. 7, pp. 1152-1162, Department of Bioengineering, Stanford University, Stanford, CA, USA.

Taylor, C.A. et al., "Patient-Specific Modeling of Cardiovascular Mechanics", Annual Review of Biomedical Engineering, 2009, pp. 109-134, Department of Bioengineering, Stanford University, Stanford, CA, USA.

Kassab, Ghassan S., "Scaling laws of vascular trees: of form and function", . Am J Physiol Heart Circ Physiol, 2006, First published Sep. 2, 2005, pp. H894-H903.

Huo, Yunlong et al., "A Scaling Law of Vascular Volume", Biophysical Journal, Jan. 2009, vol. 96, pp. 347-353, Department of Biomedical Engineering, Surgery, and Cellular and Integrative Physiology, Indiana University—Purdue University Indianapolis, Indiana, USA.

International Preliminary Report on Patentability dated Mar. 10, 2016, in corresponding International PCT Patent Application No. PCT/US2014/049562 filed Aug. 4, 2014 (8 pages).

International Search Report dated Apr. 16, 2015 in related PCT/US2014/948452; 4 pgs.

Cilia et al. (IEEE Transactions on Biomedical Engineering (2012) vol. 59, No. 4:1155-1161).

Latifoglu et al. (Journal of Biomedical Informatics (2008) vol. 41:15-23).

Motoyama et al. (Journal of the American College of Cardiology (2009) vol. 54, No. 1:49-57).

Sajda (2006) Machine learning for Detection and Diagnosis of Disease; http://liinc.bme.columbia.edu/publications/SajdaAnnReyBME.pdf, Annu. Rev. Biomol. Eng. (2006) 8:537-565.

Kononenko in Artif. Intell. Med. (2001) vol. 23(1):89-109.

\* cited by examiner

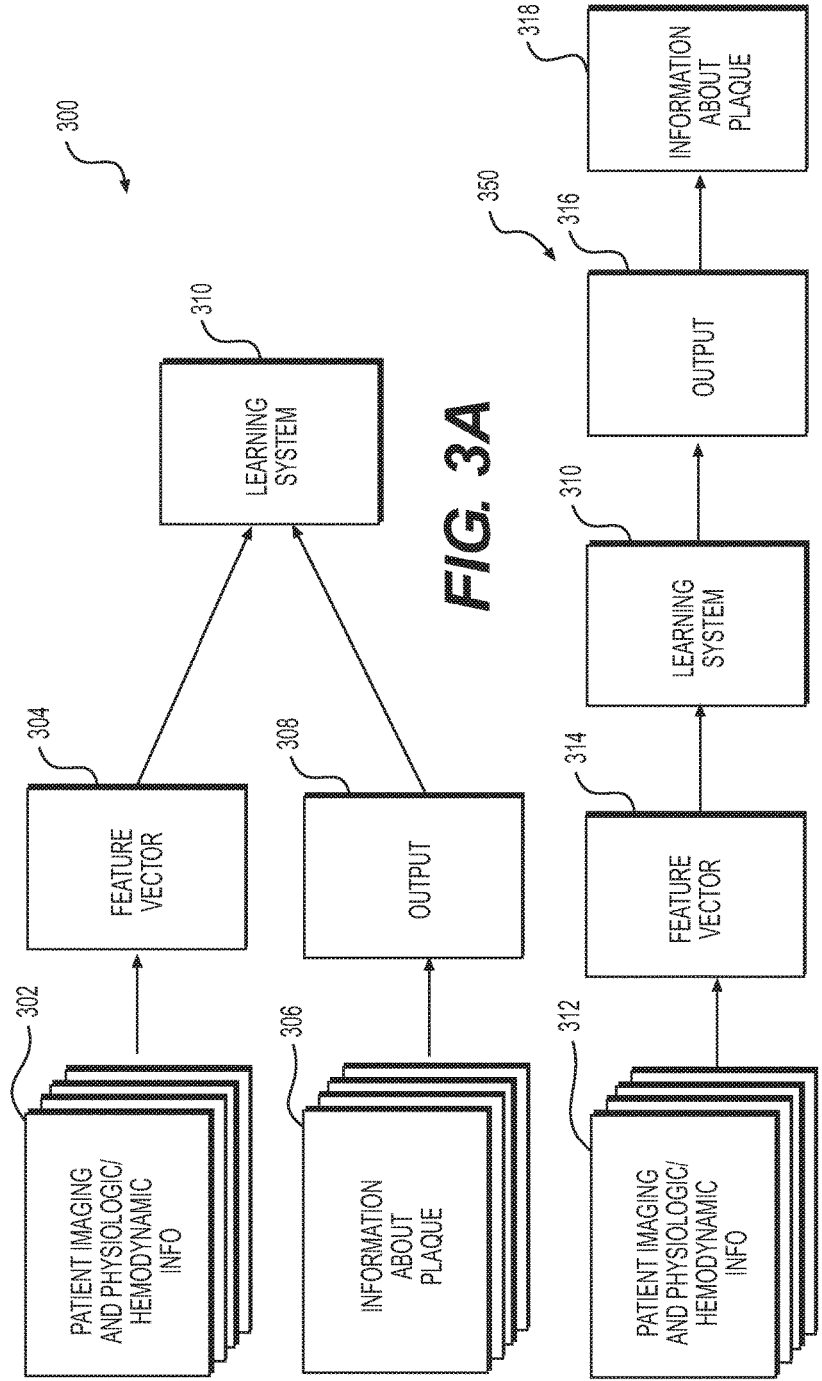

SYSTEMS AND METHODS FOR PREDICTING LOCATION, ONSET, AND/OR CHANGE OF CORONARY LESIONS

RELATED APPLICATION(S)

This application is a continuation of and claims the benefit of priority to U.S. patent application Ser. No. 14/011,151, filed Aug. 27, 2013, which is incorporated herein by reference in its entirety.

FIELD OF THE INVENTION

Various embodiments of the present disclosure relate generally to medical imaging and related methods. More specifically, particular embodiments of the present disclosure relate to systems and methods for predicting the location, onset, and/or change of coronary lesions from factors such as vessel geometry, physiology, and hemodynamics.

BACKGROUND

Coronary artery disease ("CAD") may produce coronary lesions, such as a stenosis (abnormal narrowing of a blood vessel), in the blood vessels providing blood to the heart. As a result, blood flow to the heart may be restricted. A patient suffering from coronary artery disease may experience chest pain, referred to as "chronic stable angina" during physical exertion, or "unstable angina" when the patient is at rest. A more severe manifestation of disease may lead to myocardial infarction, or heart attack.

A need exists to provide more accurate data relating to coronary lesions, e.g., size, shape, location, functional significance (e.g., whether the lesion impacts blood flow), etc. Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), positron emission tomography (PET), and coronary computed tomographic angiography (CCTA). The noninvasive tests may provide indirect evidence of coronary lesions by looking for changes in electrical activity of the heart (e.g., using electrocardiography (ECG)), motion of the myocardium (e.g., using stress echocardiography), perfusion of the myocardium (e.g., using PET or SPECT), or metabolic changes (e.g., using biomarkers). However, these noninvasive tests typically do not provide a direct assessment of coronary lesions or assess blood flow rates. Thus, patients may also require an invasive test, such as diagnostic cardiac catheterization, to visualize coronary lesions. Diagnostic cardiac catheterization may include performing conventional coronary angiography (CCA) to gather anatomic data on coronary lesions by providing a doctor with an image of the size and shape of the arteries.

However, both invasive and noninvasive tests for CAD are only useful in determining an amount of disease and/or risk of heart attack that has already been incurred. That is, tests for CAD are unable to predict future amounts of plaque build-up, stenosis, or other CAD that is likely to occur based on other known characteristics of an individual. Even though CAD is known to be associated with various risk factors, including smoking, diabetes, hypertension, and dietary habits, no techniques exist for predicting the onset of CAD. In addition, no techniques exist for predicting the type or location of plaque that is likely to develop in view of other known characteristics of an individual.

Consequently, the present disclosure describes new approaches for predicting the location, onset, and/or change of coronary lesions from factors such as vessel geometry, physiology, and hemodynamics.

SUMMARY

Systems and methods are disclosed for predicting the location, onset, and/or change of coronary lesions from factors such as vessel geometry, physiology, and hemodynamics.

According to one embodiment, a method is disclosed for predicting information relating to a coronary lesion. The method includes: acquiring, for each of a plurality of individuals, a geometric model, blood flow characteristics, and plaque information for at least part of the individual's vascular system; identifying, for each of a plurality of points in the geometric models, features predictive of the presence of plaque within the geometric models and blood flow characteristics of the plurality of individuals; training a machine learning algorithm based on the geometric models and blood flow characteristics for each of the plurality of individuals, and the predictive features; acquiring, for a patient, a geometric model and blood flow characteristics for at least part of the patient's vascular system; and executing the machine learning algorithm on the patient's geometric model and blood flow characteristics to determine, based on the predictive features, plaque information of the patient for at least one point in the patient's geometric model.

According to another embodiment, a system is disclosed for predicting information relating to a coronary lesion. The system includes a data storage device storing instructions for predicting information relating to a coronary lesion; and a processor configured to execute the instructions to perform a method including the steps of: acquiring, for each of a plurality of individuals, a geometric model, blood flow characteristics, and plaque information for at least part of the individual's vascular system; identifying, for each of a plurality of points in the geometric models, features predictive of the presence of plaque within the geometric models and blood flow characteristics of the plurality of individuals; training a machine learning algorithm based on the geometric models and blood flow characteristics for each of the plurality of individuals, and the predictive features; acquiring, for a patient, a geometric model and blood flow characteristics for at least part of the patient's vascular system; and executing the machine learning algorithm on the patient's geometric model and blood flow characteristics to determine, based on the predictive features, plaque information of the patient for at least one point in the patient's geometric model.

According to another embodiment, a non-transitory computer-readable medium is disclosed storing instructions that, when executed by a computer, cause the computer to perform a method for predicting information relating to a coronary lesion, the method including: acquiring, for each of a plurality of individuals, a geometric model, blood flow characteristics, and plaque information for at least part of the individual's vascular system; identifying, for each of a plurality of points in the geometric models, features predictive of the presence of plaque within the geometric models and blood flow characteristics of the plurality of individuals; training a machine learning algorithm based on the geometric models and blood flow characteristics for each of the plurality of individuals, and the predictive features; acquiring, for a patient, a geometric model and blood flow characteristics for at least part of the patient's vascular system; and executing the machine learning algorithm on the patient's geometric model and blood flow characteristics to determine, based on the predictive features, plaque information of the patient for at least one point in the patient's geometric model.

According to another embodiment, a computer-implemented method is disclosed for predicting information relating to a coronary lesion. One method includes acquiring, over a network, for a patient, a geometric model and blood flow characteristics for at least part of the patient's vascular system; and determining plaque information of the patient for at least one point in the patient's geometric model by executing on the patient's geometric model and blood flow characteristics, a machine learning algorithm trained based on plaque predictive features derived from geometric models, blood flow characteristics, and plaque information obtained for each of a plurality of individuals.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 3A is a block diagram of an exemplary method of training a machine learning system for predicting the location, onset, and/or change of coronary lesions from factors such as vessel geometry, physiology, and hemodynamics s, according to an exemplary embodiment of the present disclosure.

FIG. 3B is a block diagram of an exemplary method of using a trained machine learning system for predicting the location, onset, and/or change of coronary lesions from factors such as vessel geometry, physiology, and hemodynamics, according to an exemplary embodiment of the present disclosure.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

The present disclosure describes an approach for providing prognosis of coronary artery disease ("CAD") and for predicting plaque growth/shrinkage based on patient-specific geometry and blood flow characteristics. Specifically, the present disclosure describes a system that receives patient information (e.g., 3D cardiac imaging, patient demographics, and history) and provides a patient-specific and location-specific risk score for the pathogenesis of CAD. Although the present disclosure is described with particular reference to coronary artery disease, the same systems and methods are applicable to creating a patient-specific prediction of lesion formation in other vascular systems beyond the coronary arteries.

More specifically, the present disclosure describes certain principles and embodiments for using patients' cardiac imaging to: (1) derive a patient-specific geometric model of the coronary vessels; and (2) perform coronary flow simulation to extract hemodynamic characteristics, patient physiological information, and boundary conditions in order to predict the onset and location of coronary lesions. The present disclosure is not limited to a physics-based simulation of blood flow to predict the locations predisposed to plaque formation, but rather uses machine learning to predict the lesion location by incorporating various risk factors, including patient demographics and coronary geometry, as well as the results of patient-specific biophysical simulations (e.g., hemodynamic characteristics). If additional diagnostic test results are available, those results may also be used in the training and prediction. According to certain embodiments, the presently disclosed methods involve two phases: (1) a training phase in which the machine learning system is trained to predict one or more locations of coronary lesions, and (2) a production phase in which the machine learning system is used to produce one or more locations of coronary lesions.

Figure 1:
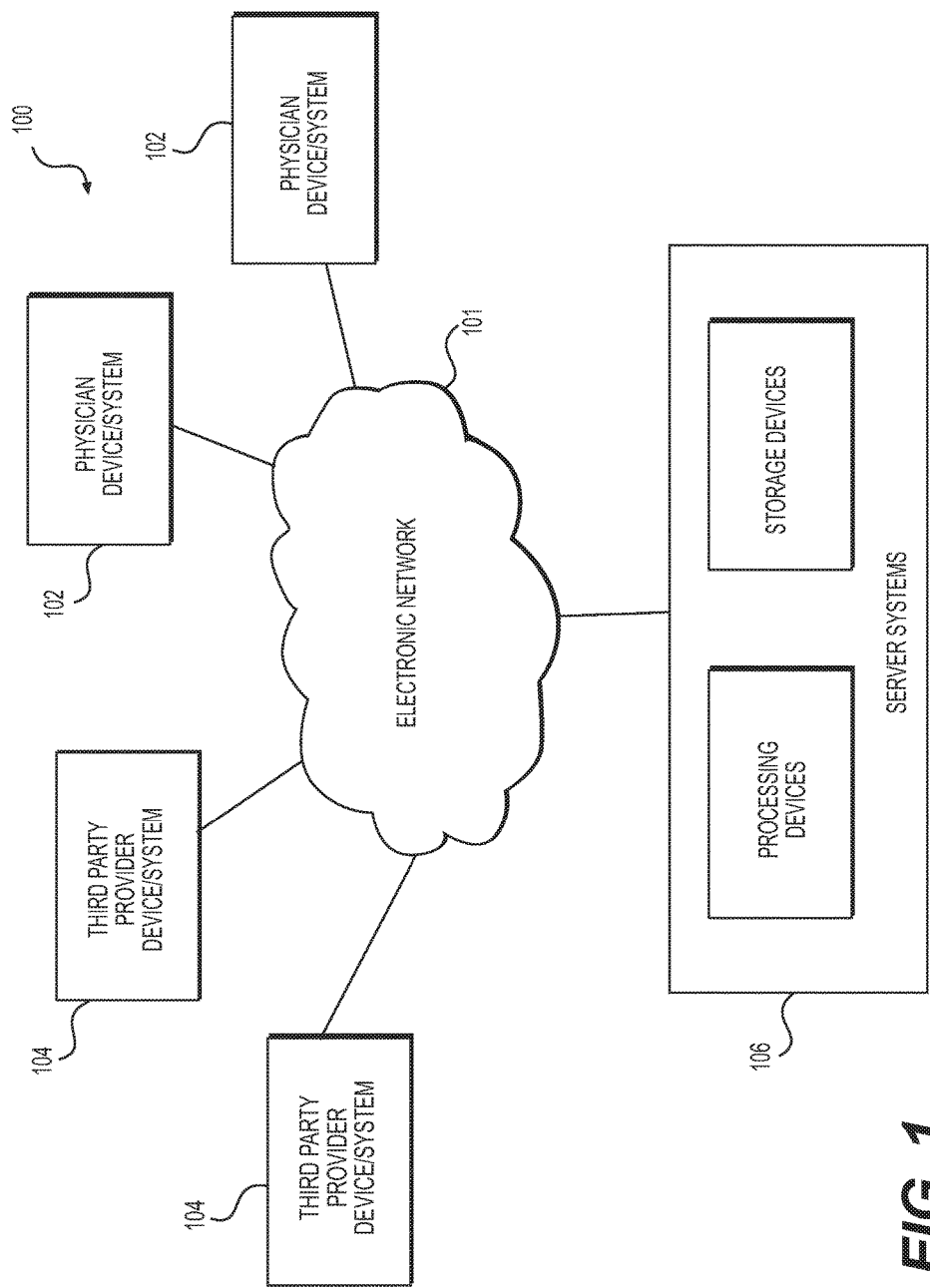
FIG. 1 is a block diagram of an exemplary system and network for predicting the location, onset, and/or change of coronary lesions from factors such as vessel geometry, physiology, and hemodynamics, according to an exemplary embodiment of the present disclosure.

Referring now to the figures, FIG. 1 depicts a block diagram of an exemplary system and network for predicting the location, onset, and/or change of coronary lesions from vessel geometry, physiology, and hemodynamics. Specifically, FIG. 1 depicts a plurality of physician devices or systems 102 and third party provider devices or systems 104, any of which may be connected to an electronic network 101, such as the Internet, through one or more computers, servers, and/or handheld mobile devices. Physicians and/or third party providers associated with physician devices or systems 102 and/or third party provider devices or systems 104, respectively, may create or otherwise obtain images of one or more patients' cardiac and/or vascular systems. The physicians and/or third party providers may also obtain any combination of patient-specific information, such as age, medical history, blood pressure, blood viscosity, etc. Physicians and/or third party providers may transmit the cardiac/vascular images and/or patient-specific information to server systems 106 over the electronic network 101. Server systems 106 may include storage devices for storing images and data received from physician devices or systems 102 and/or third party provider devices or systems 104. Server systems 106 may also include processing devices for processing images and data stored in the storage devices.

Figure 2:
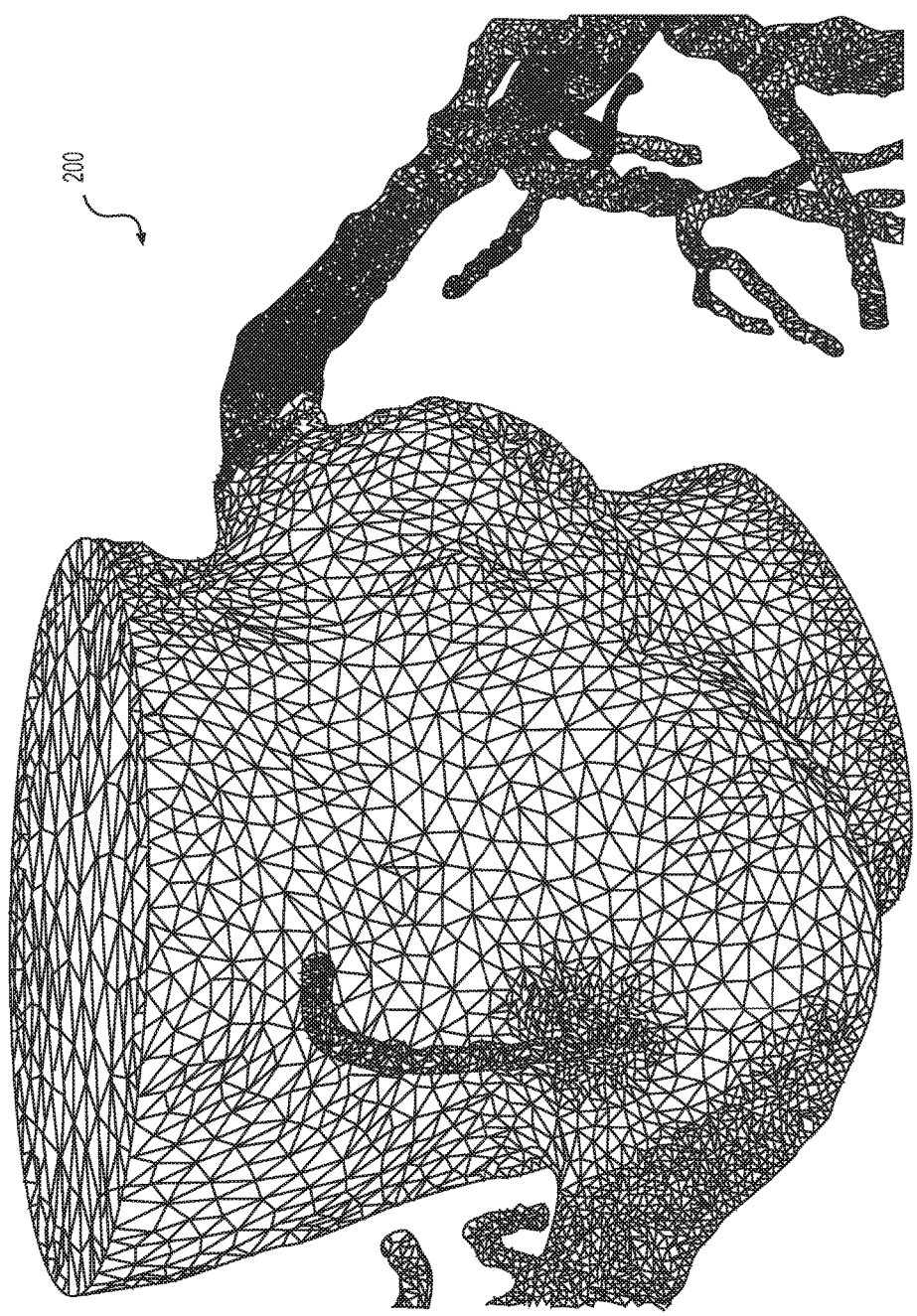
FIG. 2 is a diagram of an exemplary three-dimensional mesh of a geometric model used in predicting the location, onset, and/or change of coronary lesions from factors such as vessel geometry, physiology, and hemodynamics, according to an exemplary embodiment of the present disclosure.

FIG. 2 is a diagram of an exemplary three-dimensional mesh of a geometric model 200 used in predicting the location, onset, and/or change of coronary lesions from vessel geometry, according to an exemplary embodiment of the present disclosure. For example, as described above, a third party provider or physician may obtain patient-specific anatomical data of one or more patients. Patient-specific anatomical data may include data regarding the geometry of the patient's heart, e.g., at least a portion of the patient's aorta, a proximal portion of the main coronary arteries (and the branches extending therefrom) connected to the aorta, and the myocardium. However, as-described above, patient-specific anatomical data may also or alternatively be obtained in relation to any portion of the patient's vasculature, including beyond the patient's heart.

Initially, a patient may be selected, e.g., when the physician determines that information about the patient's coronary blood flow is desired, e.g., if the patient is experiencing symptoms associated with coronary artery disease, such as chest pain, heart attack, etc. The patient-specific anatomical data may be obtained noninvasively, e.g., using a noninvasive imaging method. For example, CCTA is an imaging method in which a user may operate a computer tomography (CT) scanner to view and create images of structures, e.g., the myocardium, the aorta, the main coronary arteries, and other blood vessels connected thereto. The CCTA data may be time-varying, e.g., to show changes in vessel shape over a cardiac cycle. CCTA may be used to produce an image of the patient's heart. For example, 64-slice CCTA data may be obtained, e.g., data relating to 64 slices of the patient's heart, and assembled into a three-dimensional image.

Alternatively, other noninvasive imaging methods, such as magnetic resonance imaging (MRI) or ultrasound (US), or invasive imaging methods, such as digital subtraction angiography (DSA), may be used to produce images of the structures of the patient's anatomy. The imaging methods may involve injecting the patient intravenously with a contrast agent to enable identification of the structures of the anatomy. The resulting imaging data (e.g., provided by CCTA, MRI, etc.) may be provided by a third-party vendor, such as a radiology lab or a cardiologist, by the patient's physician, etc.

Other patient-specific anatomical data may also be determined from the patient noninvasively. For example, physiological data such as the patient's blood pressure, baseline heart rate, height, weight, hematocrit, stroke volume, etc., may be measured. The blood pressure may be the blood pressure in the patient's brachial artery (e.g., using a pressure cuff), such as the maximum (systolic) and minimum (diastolic) pressures.

The patient-specific anatomical data obtained as described above may be transferred over a secure communication line (e.g., via electronic network 101 of FIG. 1). For example, the data may be transferred to server systems 106 or other computer system for performing computational analysis, e.g., the computational analysis described below with respect to FIGS. 3-5B. In one exemplary embodiment, the patient-specific anatomical data may be transferred to server systems 106 or other computer system operated by a service provider providing a web-based service. Alternatively, the data may be transferred to a computer system operated by the patient's physician or other user.

In one embodiment, server systems 106 may generate a three-dimensional solid model and/or three-dimensional mesh 200 based on the received patient-specific anatomical data. For example, server systems 106 may generate the three-dimensional model and/or mesh based on any of the techniques described in U.S. Pat. No. 8,315,812 by Taylor et al., which issued on Nov. 20, 2012, the entirety of which is hereby incorporated herein by reference.

FIG. 3A is a block diagram of an exemplary method 300 for training a machine learning system, based on a plurality of patients' blood flow characteristics and geometry, for predicting the location, onset, and/or change of coronary lesions from vessel geometry, physiology, and hemodynamics, according to an exemplary embodiment of the present disclosure. Specifically, as shown in FIG. 3A, method 300 may include obtaining patient imaging data (e.g., a geometric model) and physiologic and/or hemodynamic information 302 for a plurality of patients. Method 300 may include generating feature vectors 304 based on the plurality of patients' imaging and physiologic and/or hemodynamic information. Method 300 further includes obtaining information about plaque 306 for the plurality of patients, and formatting the information about the plurality of patients' plaque into the format that is desired of the output 308 of the learning system. Method 300 completes the training mode by inputting into a learning system 310 both the feature vectors 304 formed from the plurality of patients' imaging data and physiologic and/or hemodynamic information, and the output 308 of the information about plaque for the plurality of patients. For example, as will be described in more detail below, any suitable type of machine learning system may process both the feature vectors 304 and outputs 308 to identify patterns and conclusions from that data, for later use in producing outputs of information about a particular user's plaque.

FIG. 3B is a block diagram of an exemplary method 350 for using the trained machine learning system 310 for predicting, for a particular patient, the location, onset, and/or change of coronary lesions from vessel geometry, physiology, and hemodynamics, according to an exemplary embodiment of the present disclosure. As shown in FIG. 3B, method 350 may include obtaining patient imaging data (e.g., a geometric model) and physiologic and/or hemodynamic information 312 for a particular patient, for whom it is desired to predict plaque location, onset, and/or change based on the trained learning system 310. Of course, method 350 may include obtaining the patient imaging data and physiologic and/or hemodynamic information for any number of patients for whom it is desired to predict plaque location, onset, and/or change based on the trained learning system. Method 350 may include generating a feature vector 314 for each of a plurality of points of the patient's geometric model, based on one or more elements of the received physiologic and/or hemodynamic information. Method 350 may then include operating the machine learning system 310 on the feature vectors generated for the patient to obtain an output 316 of the estimates of the presence or onset of plaque at each of a plurality of points in the patient's geometric model, and translating the output into useable information 318 about the location, onset, and/or change of plaque in the patient 318.

Described below are exemplary embodiments for implementing a training mode method 300 and a production mode method 350 of machine learning for predicting the location, onset, and/or change of coronary lesions from vessel geometry, physiology, and hemodynamics, e.g. using server systems 106, based on images and data received from physicians and/or third party providers over electronic network 101. Specifically, the methods of FIGS. 4A-5B may be performed by server systems 106, based on information received from physician devices or systems 102 and/or third party provider devices or systems 104 over electronic network 101.

Figure 4A:
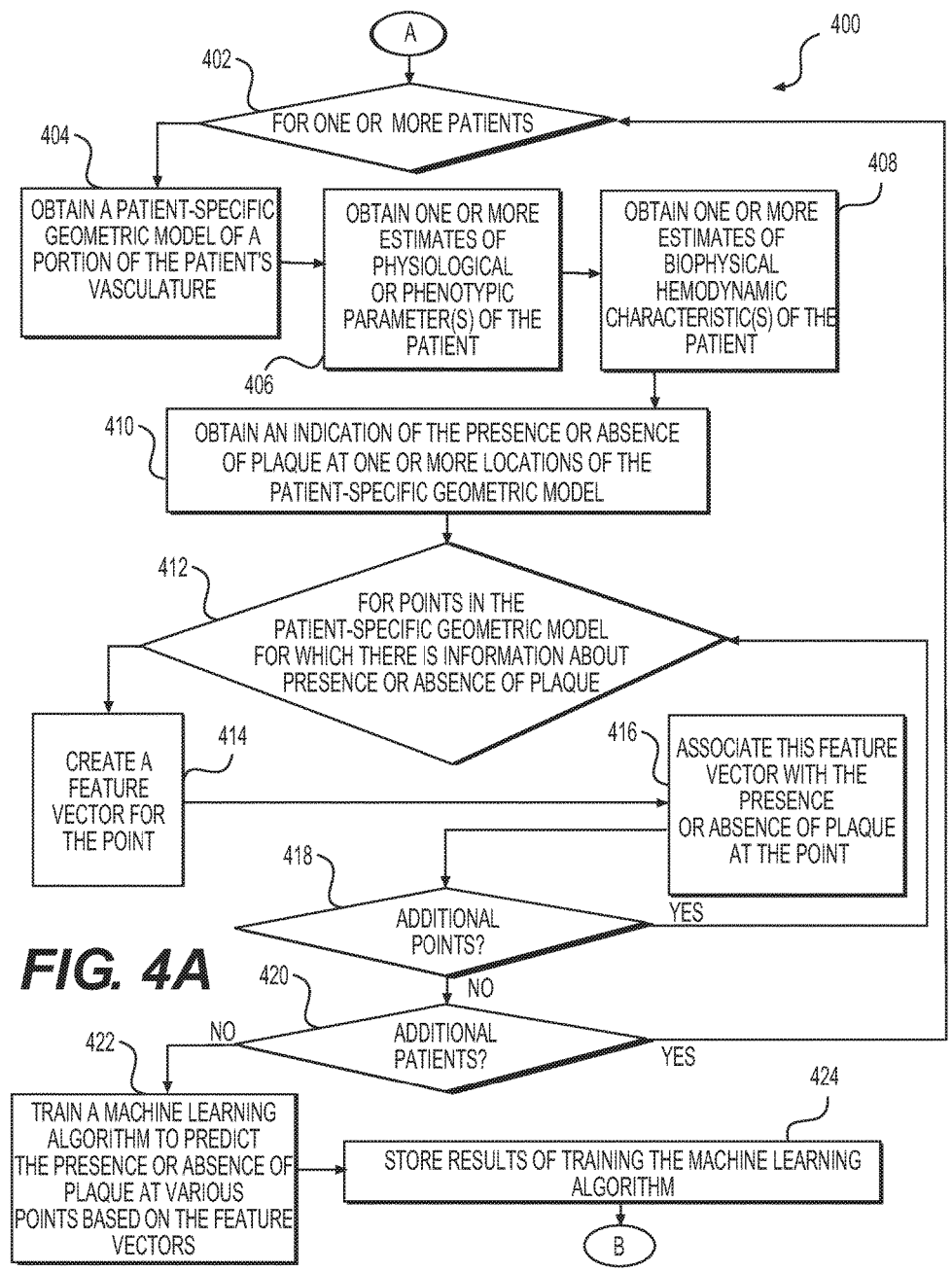
FIG. 4A is a block diagram of an exemplary method of training a machine learning system for predicting the location of coronary lesions from factors such as vessel geometry, physiology, and hemodynamics, according to an exemplary embodiment of the present disclosure.

FIG. 4A is a block diagram of an exemplary method 400 for training a machine learning system (e.g., a machine learning system 310 executed on server systems 106) for predicting the location of coronary lesions from vessel geometry, physiology, and hemodynamics, according to an exemplary embodiment of the present disclosure. Specifically, method 400 may include, for one or more patients (step 402), obtaining a patient-specific geometric model of a portion of the patient's vasculature (step 404), obtaining one or more estimates of physiological or phenotypic parameters of the patient (step 406), and obtaining one or more estimates of biophysical hemodynamic characteristics of the patient (step 408).

For example, the step of obtaining a patient-specific geometric model of a portion of the patient's vasculature (step 404) may include obtaining a patient-specific model of the geometry for one or more of the patient's blood vessels, myocardium, aorta, valves, plaques, and/or chambers. In one embodiment, this geometry may be represented as a list of points in space (possibly with a list of neighbors for each point) in which the space can be mapped to spatial units between points (e.g., millimeters). In one embodiment, this model may be derived by performing a cardiac CT imaging of the patient in the end diastole phase of the cardiac cycle. This image then may be segmented manually or automatically to identify voxels belonging to the aorta and the lumen of the coronary arteries. Given a 3D image of coronary vasculature, any of the many available methods may be used for extracting a patient-specific model of cardiovascular geometry. Inaccuracies in the geometry extracted automatically may be corrected by a human observer who compares the extracted geometry with the images and makes corrections as needed. Once the voxels are identified, the geometric model can be derived (e.g., using marching cubes).

The step of obtaining one or more estimates of physiological or phenotypic parameters of the patient (step 406) may include obtaining a list of one or more estimates of physiological or phenotypic parameters of the patient, such as blood pressure, blood viscosity, in vitro blood test results (e.g., LDL/Triglyceride cholesterol level), patient age, patient gender, the mass of the supplied tissue, etc. These parameters may be global (e.g., blood pressure) or local (e.g., estimated density of the vessel wall at a location). In one embodiment, the physiological or phenotypic parameters may include, blood pressure, hematocrit level, patient age, patient gender, myocardial mass (e.g., derived by segmenting the myocardium in the image, and calculating the volume in the image and using an estimated density of 1.05 g/mL to estimate the myocardial mass), general risk factors of coronary artery disease (e.g., smoking, diabetes, hypertension, abdominal obesity, dietary habits, family history, etc.), and/or in vitro blood test results (e.g., LDL, Triglyceride cholesterol level).

The step of obtaining one or more estimates of biophysical hemodynamic characteristics of the patient (step 408) may include obtaining a list of one or more estimates of biophysical hemodynamic characteristics from computational fluid dynamics analysis, such as wall-shear stress, oscillatory shear index, particle residence time, Reynolds number, Womersley number, local flow rate, and turbulent kinetic energy, etc. Specifically, the mean wall-shear stress, may be defined as $$\left| \frac{1}{T_1 - T_0} \int_{T_0}^{T_1} \vec{t}_s dt \right|.$$

$\vec{t}_s$, which may be the wall shear stress vector defined as the in-plane component of the surface traction vector. The oscillatory shear index (OSI), may be defined as $$\frac{1}{2}\left(1 - \frac{\left|\frac{1}{T_1 - T_0} \int_{T_0}^{T_1} \vec{t}_s dt\right|}{\frac{1}{T_1 - T_0} \int_{T_0}^{T_1} |\vec{t}_s| dt}\right),$$

which may be a measure of the uni-directionality of shear stress. The particle residence time may be a measure of the time it takes blood to be flushed from a specified fluid domain. The turbulent kinetic energy ("TKE") may be a measure of the intensity of turbulence associated with eddies in turbulent flow, and may be characterized by measured root-mean-square velocity fluctuation, and may be normalized by kinetic energy. The Reynolds number may be defined as $$\frac{\rho U D}{\mu}$$

where ($\rho$: density of blood, U: average flow velocity, D: vessel diameter, $\mu$: dynamic viscosity). The Womersley number may be defined as $$\frac{D}{2}\sqrt{\frac{\bar{\omega}\rho}{\mu}}$$

where ($\bar{\omega}$: angular frequency, equal to $$\frac{1}{\text{cardiac cycle length}}\bigg).$$

Method 400 may further include obtaining an indication of the presence or absence of plaque at one or more locations of the patient-specific geometric model (step 410). For example, in one embodiment, the location of calcified or non-calcified plaque may be determined using CT and/or other imaging modalities, including intravascular ultrasound, or optical coherence tomography. For example, the plaque may be detected in the three-dimensional image (200 of FIG. 2) generated from patient-specific anatomical data. The plaque may be identified in a three-dimensional image or model as areas that are lighter than the lumens of the aorta, the main coronary arteries, and/or the branches. Thus, the plaque may be detected by the computer system as having an intensity value below a set value or may be detected visually by the user. The location of detected plaques may be parameterized by a distance from the ostium point (left main or right coronary ostium) to the projection of centroid of plaque coordinates onto the associated vessel centerline and an angular position of plaque with respect to myocardium (e.g., myocardial/pericardial side). The location of detected plaques may be also parameterized by start and end points of the projection of plaque coordinates onto the associated vessel centerline. If plaque exists at a location, method 400 may include obtaining a list of one or more measurements of coronary plaque composition, e.g., type, Hounsfield units ("HU"), etc., burden, shape (eccentric or concentric), and location.

Method 400 may further include, for each of a plurality of points in the patient-specific geometric model for which there is information about the presence or absence of plaque (step 412), creating a feature vector for the point (step 414) and associating the feature vector with the presence or absence of plaque at that point (step 416). In one embodiment, the step of creating a feature vector for the point may include creating a feature vector for that point that consists of a numerical description of the geometry and biophysical hemodynamic characteristics at that point, and estimates of physiological or phenotypic parameters of the patient. For example, a feature vector for attributes: distance to ostium, wall shear stress, local flow rate, Reynolds number, and centerline curvature, may be in the form of (50 mm, 70 dyne/cm$^2$, 1500 mm$^3$/sec, 400, 1 mm$^{-1}$). Global physiological or phenotypic parameters may be used in the feature vector of all points, and local physiological or phenotypic parameters may change in the feature vector of different points.

In one embodiment, an exemplary feature vector generated in step 414 may include one or more of: (i) systolic and diastolic blood pressure, (ii) heart rate, (iii) blood properties including: plasma, red blood cells (erythrocytes), hematocrit, white blood cells (leukocytes) and platelets (thrombocytes), viscosity, yield stress, etc. (iv) patient age, gender, height, weight, etc., (v) lifestyle characteristics, e.g., presence or absence of current medications/drugs, (vi) general risk factors of CAD, such as smoking, diabetes, hypertension, abdominal obesity, dietary habits, family history of CAD, etc., (vii) in vitro blood test results, such as LDL, Triglyceride cholesterol level, etc., (viii) coronary calcium score, (ix) amount of calcium in aorta and valve, (x) presence of aortic aneurysm, (xi) presence of valvular heart disease, (xii) presence of peripheral disease, (xiii) presence of dental disease, (xiv) epicardial fat volume, (xv) cardiac function (ejection fraction), (xvi) stress echocardiogram test results, (xvii) characteristics of the aortic geometry (e.g., cross-sectional area profile along the ascending and descending aorta, and surface area and volume of the aorta, (xviii) a SYNTAX score, as described in U.S. patent application Ser. No. 13/656,183, filed by Timothy A. Fonte et al. on Oct. 19, 2012, the entire disclosure of which is incorporated herein by reference, (xix) plaque burden of existing plaque, (xx) adverse plaque characteristics of existing plaque (e.g., presence of positive remodeling, presence of low attenuation plaque, presence of spotty calcification), (xxi) characteristics of the coronary branch geometry, (xxii) characteristics of coronary cross-sectional area, (xxiii) characteristics of coronary lumen intensity, e.g., intensity change along the centerline (slope of linearly-fitted intensity variation), (xxiv) characteristics of surface of coronary geometry, e.g., 3D surface curvature of geometry (Gaussian, maximum, minimum, mean), (xxv) characteristics of volume of coronary geometry, e.g., ratio of total coronary volume compared to myocardial volume, (xxvi) characteristics of coronary centerline, (xxvii) characteristics of coronary deformation, (xxviii) characteristics of existing plaque, and (xxix) characteristics of coronary hemodynamics derived from computational flow dynamics or invasive measurement.

In one embodiment, the characteristics of the coronary branch geometry may include one or more of: (1) total number of vessel bifurcations, and the number of upstream/downstream vessel bifurcations; (2) average, minimum, and maximum upstream/downstream cross-sectional areas; (3) distances (along the vessel centerline) to the centerline point of minimum and maximum upstream/downstream cross-sectional areas, (4) cross-sectional area of and distance (along the vessel centerline) to the nearest upstream/downstream vessel bifurcation, (5) cross-sectional area of and distance (along the vessel centerline) to the nearest coronary outlet and aortic inlet/outlet, (6) cross-sectional areas and distances (along the vessel centerline) to the downstream coronary outlets with the smallest/largest cross-sectional areas, and/or (7) upstream/downstream volumes of the coronary vessels.

In one embodiment, the characteristics of coronary cross-sectional area may include one or more of: (1) cross-sectional lumen area along the coronary centerline, (2) cross-sectional lumen area to the power of N (where N can be determined from various source of scaling laws such as Murray's law (N=1.5) and Uylings' study (N=1.165~1.5)), (3) a ratio of lumen cross-sectional area with respect to the main ostia (LM, RCA) (e.g., measure of cross-sectional area at the LM ostium, normalized cross-sectional area of the left coronary by LM ostium area, measure of cross-sectional area at the RCA ostium, normalized cross-sectional area of the right coronary by RCA ostium area), (4) ratio of lumen cross-sectional area with respect to the main ostia to the power of N (where N can be determined from various sources of scaling laws such as Murray's law (N=1.5) and Uyling's study (N=1.165~1.5)), (5) degree of tapering in cross-sectional lumen area along the centerline (based on a sample centerline points within a certain interval (e.g., twice the diameter of the vessel) and computation of a slope of linearly-fitted cross-sectional area), (6) location of stenotic lesions (based on detecting minima of cross-sectional area curve (e.g., detecting locations, where first derivative of area curve is zero and second derivative is positive, and smoothing cross-sectional area profile to avoid detecting artifactual peaks), and computing distance (parametric arc length of centerline) from the main ostium, (7) length of stenotic lesions (computed based on the proximal and distal locations from the stenotic lesion, where cross-sectional area is recovered), (8) degree of stenotic lesions, by evaluating degree of stenosis based on reference values of smoothed cross-sectional area profile using Fourier smoothing or kernel regression, (9) location and number of lesions corresponding to 50%, 75%, 90% area reduction, (10) distance from stenotic lesion to the main ostia, and/or (11) irregularity (or circularity) of cross-sectional lumen boundary.

In one embodiment, the characteristics of coronary centerline may include: (1) curvature (bending) of coronary centerline, such as by computing Frenet curvature, based on $$\kappa = \frac{|p' \times p''|}{|p'|^3},$$

where ρ is a coordinate of the centerline, and computing an inverse of the radius of a circumscribed circle along the centerline points, and (2) tortuosity (non-planarity) of coronary centerline, such as by computing Frenet torsion, based on $$\tau = \frac{(p' \times p'') \cdot p'''}{|p' \times p''|^2},$$

where ρ is a coordinate of the centerline.

In one embodiment, calculation of the characteristics of coronary deformation may involve multi-phase CCTA (e.g., diastole and systole), including (1) distensibility of coronary artery over cardiac cycle, (2) bifurcation angle change over cardiac cycle, and/or (3) curvature change over cardiac cycle. In one embodiment, the characteristics of existing plaque may be calculated based on: (1) volume of plaque, (2) intensity of plaque, (3) type of plaque (calcified, non-calcified), (4) distance from the plaque location to ostium (LM or RCA), and (5) distance from the plaque location to the nearest downstream/upstream bifurcation.

In one embodiment, the characteristics of coronary hemodynamics may be derived from computational flow dynamics or invasive measurement. For example, pulsatile flow simulation may be performed to obtain transient characteristics of blood, by using a lumped parameter coronary vascular model for downstream vasculatures, inflow boundary condition with coupling a lumped parameter heart model and a closed loop model to describe the intramyocardial pressure variation resulting from the interactions between the heart and arterial system during cardiac cycle. For example, the calculation may include: measured FFR, coronary flow reserve, pressure distribution, FFRct, mean wall-shear stress, oscillatory shear index, particle residence time, turbulent kinetic energy, Reynolds number, Womersley number, and/or local flow rate.

Method 400 may then include associating the feature vector with the presence or absence of plaque at each point of the patient-specific geometric model (step 416). Method 400 may involve continuing to perform the above steps 412, 414, 416, for each of a plurality of points in the patient-specific geometric model (step 418), and for each of any number of patients on which a machine learning algorithm may be based (step 420). Method 400 may then include training the machine learning algorithm to predict the probability of the presence of plaque at the points from the feature vectors at the points (step 422). Examples of machine learning algorithms suitable for performing this task may include support vector machines (SVMs), multi-layer perceptrons (MLPs), and/or multivariate regression (MVR) (e.g., weighted linear or logistic regression).

Method 400 may then include storing or otherwise saving the results of the machine learning algorithm (e.g., feature weights) to a digital representation, such as the memory or digital storage (e.g., hard drive, network drive) of a computational device, such as a computer, laptop, DSP, server, etc. of server systems 106 (step 424).

Figure 4B:
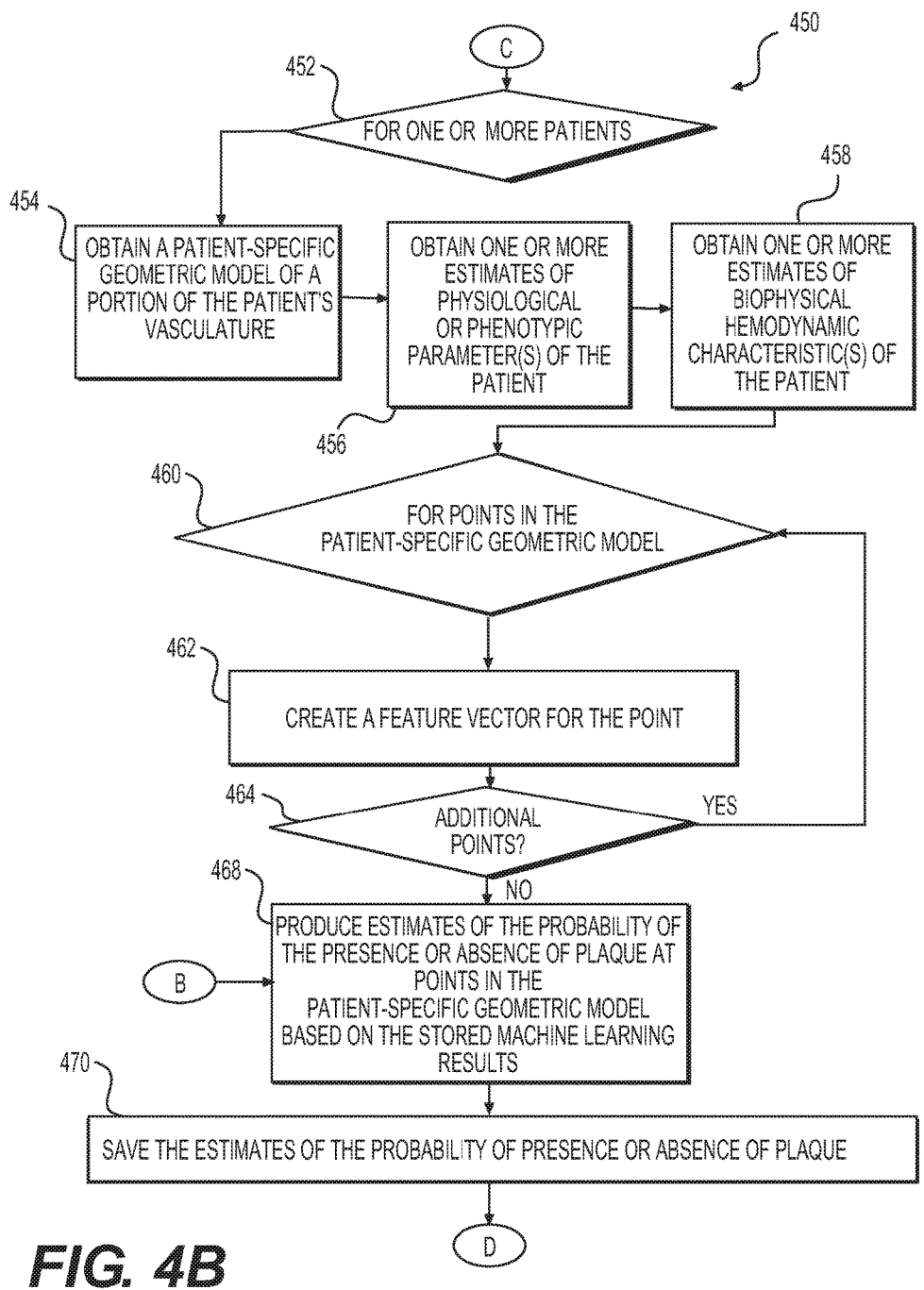
FIG. 4B is a block diagram of an exemplary method of using a trained machine learning system for predicting the location of coronary lesions from factors such as vessel geometry, physiology, and hemodynamics, according to an exemplary embodiment of the present disclosure.

FIG. 4B is a block diagram of an exemplary method 450 for using a machine learning system trained according to method 400 (e.g., a machine learning system 310 executed on server systems 106) for predicting, for a particular patient, the location of coronary lesions from vessel geometry, physiology, and hemodynamics, according to an exemplary embodiment of the present disclosure. In one embodiment, method 450 may include, for one or more patients (step 452), obtaining a patient-specific geometric model of a portion of the patient's vasculature (step 454), obtaining one or more estimates of physiological or phenotypic parameters of the patient (step 456), and obtaining one or more estimates of biophysical hemodynamic characteristics of the patient (step 458).

Specifically, the step of obtaining a patient-specific geometric model of a portion of the patient's vasculature (step 454) may include obtaining a patient-specific model of the geometry for one or more of the patient's blood vessels, myocardium, aorta, valves, plaques, and/or chambers. In one embodiment, this geometry may be represented as a list of points in space (possibly with a list of neighbors for each point) in which the space can be mapped to spatial units between points (e.g., millimeters). In one embodiment, this model may be derived by performing a cardiac CT imaging of the patient in the end diastole phase of the cardiac cycle. This image then may be segmented manually or automatically to identify voxels belonging to the aorta and the lumen of the coronary arteries. Inaccuracies in the geometry extracted automatically may be corrected by a human observer who compares the extracted geometry with the images and makes corrections as needed. Once the voxels are identified, the geometric model can be derived (e.g., using marching cubes).

In one embodiment, the step of obtaining one or more estimates of physiological or phenotypic parameters of the patient (step 456) may include obtaining a list of one or more estimates of physiological or phenotypic parameters of the patient, such as blood pressure, blood viscosity, in vitro blood test results (e.g., LDL/Triglyceride cholesterol level), patient age, patient gender, the mass of the supplied tissue, etc. These parameters may be global (e.g., blood pressure) or local (e.g., estimated density of the vessel wall at a location). In one embodiment, the physiological or phenotypic parameters may include, blood pressure, hematocrit level, patient age, patient gender, myocardial mass (e.g., derived by segmenting the myocardium in the image, and calculating the volume in the image and using an estimated density of 1.05 g/mL to estimate the myocardial mass), general risk factors of coronary artery disease (e.g., smoking, diabetes, hypertension, abdominal obesity, dietary habits, family history, etc.), and/or in vitro blood test results (e.g., LDL, Triglyceride cholesterol level).

In one embodiment, the step of obtaining one or more estimates of biophysical hemodynamic characteristics of the patient (step 458) may include obtaining a list of one or more estimates of biophysical hemodynamic characteristics from computational fluid dynamics analysis, such as wall-shear stress, oscillatory shear index, particle residence time, Reynolds number, Womersley number, local flow rate, and turbulent kinetic energy, etc. Specifically, the mean wall-shear stress, may be defined as $$\left| \frac{1}{T_1 - T_0} \int_{T_0}^{T_1} \vec{t}_s dt \right| \cdot \vec{t}_s,$$

which may be the wall shear stress vector defined as the in-plane component of the surface traction vector. The oscillatory shear index (OSI), may be defined as $$\frac{1}{2}\left(1 - \frac{\left|\frac{1}{T_1 - T_0}\int_{T_0}^{T_1} \vec{t_s} dt\right|}{\frac{1}{T_1 - T_0}\int_{T_0}^{T_1} |\vec{t_s}| dt}\right),$$

which may be a measure of the uni-directionality of shear stress. The particle residence time may be a measure of the time it takes blood to be flushed from a specified fluid domain. The turbulent kinetic energy (TKE) may be a measure of the intensity of turbulence associated with eddies in turbulent flow, and may be characterized by measured root-mean-square velocity fluctuation, and may be normalized by kinetic energy. The Reynolds number may be defined as $$\frac{\rho U D}{\mu}$$

where (ρ: density of blood, U: average flow velocity, D: vessel diameter, μ: dynamic viscosity). The Womersley number may be defined as $$\frac{D}{2}\sqrt{\frac{\varpi \rho}{\mu}}$$

where ($\varpi$: angular frequency, equal to $$\frac{1}{\text{cardiac cycle length}}\Big).$$

Method 450 may include, for every point in the patient-specific geometric model of the patient (step 460), creating for that point a feature vector comprising a numerical description of the geometry and biophysical hemodynamic characteristic at that point, and estimates of physiological or phenotypic parameters of the patient (step 462). Global physiological or phenotypic parameters may be used in the feature vector of one or more points, and local physiological or phenotypic parameters may change in the feature vector of different points. Method 450 may involve continuing to perform the above steps 460, 462, for each of a plurality of points in the patient-specific geometric model (step 464).

Method 450 may then include producing estimates of the probability of the presence or absence of plaque at each point in the patient-specific geometric model based on the stored machine learning results (stored at B, FIG. 4A) (step 468). Specifically, method 450 may use the saved results of the machine learning algorithm 310 produced in the training mode of method 400 (e.g., feature weights) to produce estimates of the probability of the presence of plaque at each point in the patient-specific geometric model (e.g., by generating plaque estimates as a function of the feature vector at each point). These estimates may be produced using the same machine learning algorithm technique used in the training mode (e.g., the SVM, MLP, MVR technique). In one embodiment, the estimates may be a probability of the existence of plaque at each point of a geometric model. If there is no existing plaque at a point, the method may include generating an estimated probability of the onset of plaque (e.g., lipid-rich, non-calcified plaque). If plaque does exist at a point, the method may include generating an estimated probability of progression of the identified plaque to a different stage (e.g., fibrotic or calcified), and the amount or shape of such progression. In one embodiment, the estimates may be a probability of a shape, type, composition, size, growth, and/or shrinkage of plaque at any given location or combination of locations. For example, in one embodiment, (in the absence of longitudinal training data) the progression of plaque may be predicted by determining that the patient appears that they should have disease characteristic X based on the patient's population, despite actually having characteristic Y. Therefore, the estimate may include a prediction that the patient will progress from state X to state Y, which may include assumptions and/or predictions about plaque growth, shrinkage, change of type, change of composition, change of shape, etc.). Method 450 may then include saving the estimates of the probability of the presence or absence of plaque (step 470), such as to the memory or digital storage (e.g., hard drive, network drive) of a computational device, such as a computer, laptop, DSP, server, etc., of server systems 106, and communicating these patient-specific and location-specific predicted probabilities of lesion formation to a health care provider, such as over electronic network 101.

Figure 5A:
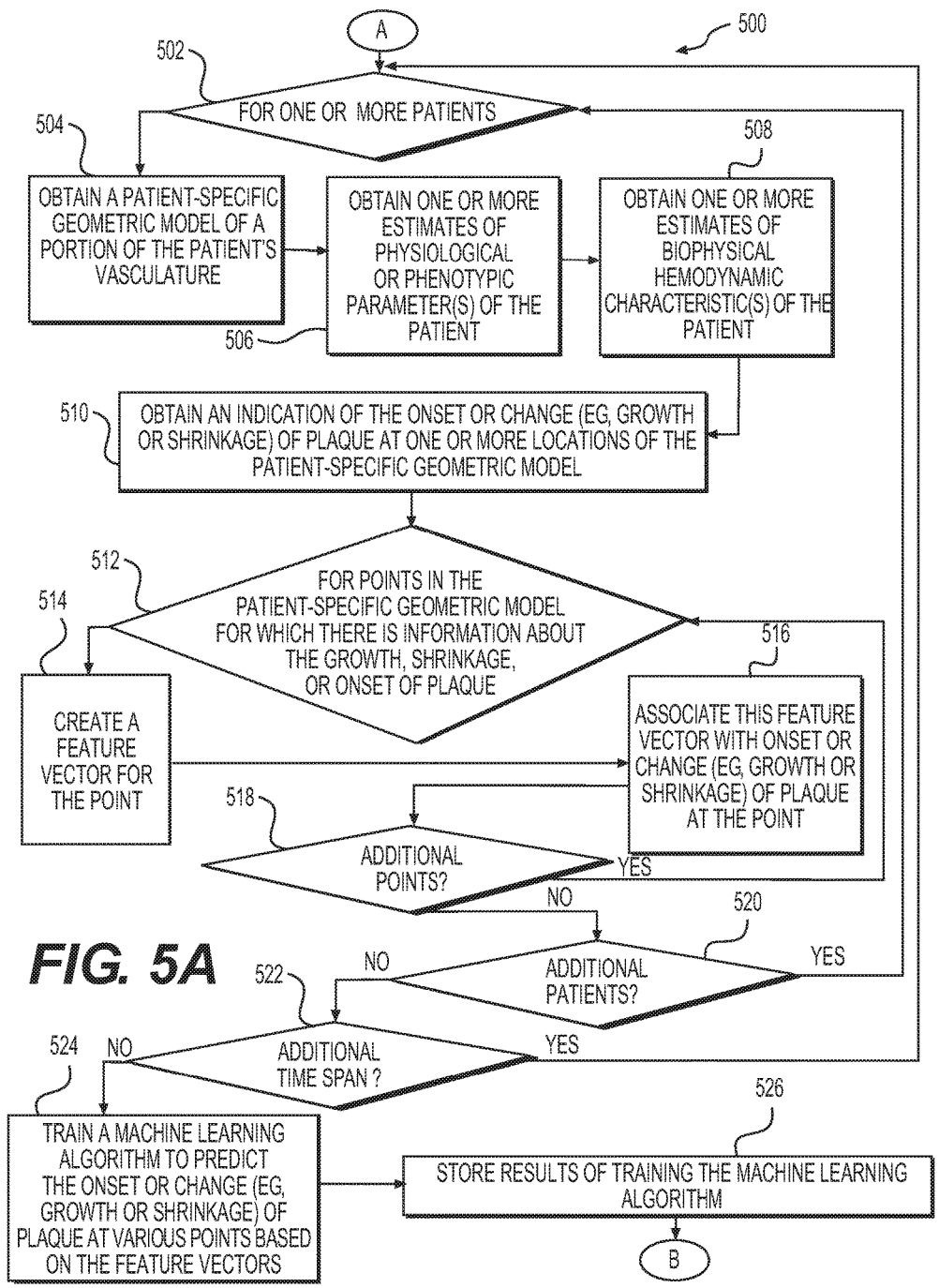
FIG. 5A is a block diagram of an exemplary method of training a machine learning system for predicting the onset and/or change (e.g., rate of growth/shrinkage) of coronary lesions from vessel geometry, physiology, and hemodynamics, according to an exemplary embodiment of the present disclosure.

FIG. 5A is a block diagram of an exemplary method 500 for training a machine learning system (e.g., a machine learning system 310 executed on server systems 106) for predicting the onset or change (e.g., growth and/or shrinkage), of coronary lesions over time, such as by using longitudinal data (i.e., corresponding data taken from the same patients at different points in time) of vessel geometry, physiology, and hemodynamics, according to an exemplary embodiment of the present disclosure. Specifically, method 500 may include, for one or more patients (step 502), obtaining a patient-specific geometric model of a portion of the patient's vasculature (step 504), obtaining one or more estimates of physiological or phenotypic parameters of the patient (step 506), and obtaining one or more estimates of biophysical hemodynamic characteristics of the patient (step 508).

For example, the step of obtaining a patient-specific geometric model of a portion of the patient's vasculature (step 504) may include obtaining a patient-specific model of the geometry for one or more of the patient's blood vessels, myocardium, aorta, valves, plaques, and/or chambers. In one embodiment, this geometry may be represented as a list of points in space (possibly with a list of neighbors for each point) in which the space can be mapped to spatial units between points (e.g., millimeters). In one embodiment, this model may be derived by performing a cardiac CT imaging of the patient in the end diastole phase of the cardiac cycle. This image then may be segmented manually or automatically to identify voxels belonging to the aorta and the lumen of the coronary arteries. Inaccuracies in the geometry extracted automatically may be corrected by a human observer who compares the extracted geometry with the images and makes corrections as needed. Once the voxels are identified, the geometric model can be derived (e.g., using marching cubes).

The step of obtaining one or more estimates of physiological or phenotypic parameters of the patient (step 506) may include obtaining a list of one or more estimates of physiological or phenotypic parameters of the patient, such as blood pressure, blood viscosity, in vitro blood test results (e.g., LDL/Triglyceride cholesterol level), patient age, patient gender, the mass of the supplied tissue, etc. These parameters may be global (e.g., blood pressure) or local (e.g., estimated density of the vessel wall at a location). In one embodiment, the physiological or phenotypic parameters may include, blood pressure, hematocrit level, patient age, patient gender, myocardial mass (e.g., derived by segmenting the myocardium in the image, and calculating the volume in the image and using an estimated density of 1.05 g/mL to estimate the myocardial mass), general risk factors of coronary artery disease (e.g., smoking, diabetes, hypertension, abdominal obesity, dietary habits, family history, etc.), and/or in vitro blood test results (e.g., LDL, Triglyceride cholesterol level).

The step of obtaining one or more estimates of biophysical hemodynamic characteristics of the patient (step 508) may include obtaining a list of one or more estimates of biophysical hemodynamic characteristics from computational fluid dynamics analysis, such as wall-shear stress, oscillatory shear index, particle residence time, Reynolds number, Womersley number, local flow rate, and turbulent kinetic energy, etc. Specifically, the mean wall-shear stress, may be defined as $$\left| \frac{1}{T_1 - T_0} \int_{T_0}^{T_1} \vec{t_s} \, dt \right|.$$

$\vec{t_s}$, which may be the wall shear stress vector defined as the in-plane component of the surface traction vector. The oscillatory shear index (OSI), may be defined as $$\frac{1}{2}\left(1 - \frac{\left|\frac{1}{T_1-T_0}\int_{T_0}^{T_1}\vec{t_s}\,dt\right|}{\frac{1}{T_1-T_0}\int_{T_0}^{T_1}|\vec{t_s}|\,dt}\right),$$

which may be a measure of the uni-directionality of shear stress. The particle residence time may be a measure of the time it takes blood to be flushed from a specified fluid domain. The turbulent kinetic energy (TKE) may be a measure of the intensity of turbulence associated with eddies in turbulent flow, and may be characterized by measured root-mean-square velocity fluctuation, and may be normalized by kinetic energy. The Reynolds number may be defined as $$\frac{\rho U D}{\mu}$$

where ($\rho$: density of blood, U: average flow velocity, D: vessel diameter, $\mu$: dynamic viscosity). The Womersley number may be defined as $$\frac{D}{2}\sqrt{\frac{\varpi \rho}{\mu}}$$

where ($\varpi$: angular frequency, equal to $$\frac{1}{\text{cardiac cycle length}}).$$

Method 500 may further include obtaining an indication of the growth, shrinkage, or onset of plaque at one or more locations of the patient-specific geometric model (step 510). For example, in one embodiment, the location of plaque may be determined using CT and/or other imaging modalities, including intravascular ultrasound, or optical coherence tomography. If plaque exists at a location, method 500 may include obtaining a list of one or more measurements of coronary plaque composition, burden and location.

In order to synchronize geometry obtained from patients over time, it may be desirable to determine point correspondence between multiple time variant scans of each individual. In other words, it may be desirable to learn the vessel characteristics in a location at the earlier time point that are correlated with the progression of disease in the same location at the later time point, such as by using a database of pairs of images of the same patient at two different time points. Given the image of a new patient, training data of local disease progression may then be used to predict the change in disease at each location. Accordingly, in one embodiment, step 510 may further include: (i) determining a mapping of a coronary centerline from an initial scan to a follow-up scan; and (ii) determining a mapping of extracted plaques using curvilinear coordinates defined along the centerline. In one embodiment, the coronary centerline mapping may be determined by (i) extracting centerlines of major epicardial coronary arteries (e.g., left descending coronary artery, circumflex artery, right coronary artery) and branch vessels (e.g, diagonal, marginal, etc) for each scan; (ii) using bifurcating points as fiducial landmarks to determine common material points between the scans; and (iii) for points between bifurcations, using linear interpolation or cross-sectional area profile (e.g., value, slope) of coronary vessels to identify correspondence. In one embodiment, the mapping of extracted plaques may be determined by: (i) extracting plaque from each scan; (ii) parameterizing the location of plaque voxels by curvilinear coordinate system for each associated centerline (r, θ, s); and determining correspondence of plaque voxels in each curvilinear coordinate system. In one embodiment, the curvilinear coordinate system may be defined where:

r=distance from plaque voxel to the associated centerline (projection of plaque);

s=distance from ostium point (Left main or right coronary) to the projection of plaque voxel onto associated centerline; and θ=angular position with respect to reference parallel path to centerline.

Method 500 may further include, for each of a plurality of points in the patient-specific geometric model for which there is information about the growth, shrinkage, or onset of plaque (step 512), creating a feature vector for the point (step 514) and associating the feature vector with the growth, shrinkage, or onset of plaque at that point (step 516). In one embodiment, the step of creating a feature vector for the point may include creating a feature vector for that point that consists of a numerical description of the geometry and biophysical hemodynamic characteristics at that point, and estimates of physiological or phenotypic parameters of the patient. For example, a feature vector for attributes: hematocrit, plaque burden, plaque Hounsfield unit, distance to ostium, wall shear stress, flow, Reynolds number, and centerline curvature may be in the form of: (45%, 20 mm$^3$, 130 HU, 60.5 mm, 70 dyne/cm$^2$, 1500 mm$^3$/sec, 400, 1 mm$^{-1}$). Global physiological or phenotypic parameters may be used in the feature vector of all points, and local physiological or phenotypic parameters may change in the feature vector of different points.

In one embodiment, an exemplary feature vector generated in step 514 may include one or more of: (i) systolic and diastolic blood pressure, (ii) heart rate, (iii) blood properties including: plasma, red blood cells (erythrocytes), hematocrit, white blood cells (leukocytes) and platelets (thrombocytes), viscosity, yield stress, etc. (iv) patient age, gender, height, weight, etc., (v) lifestyle characteristics, e.g., presence or absence of current medications/drugs, (vi) general risk factors of CAD, such as smoking, diabetes, hypertension, abdominal obesity, dietary habits, family history of CAD, etc., (vii) in vitro blood test results, such as LDL, Triglyceride cholesterol level, etc., (viii) coronary calcium score, (ix) amount of calcium in aorta and valve, (x) presence of aortic aneurysm, (xi) presence of valvular heart disease, (xii) presence of peripheral disease, (xiii) presence of dental disease, (xiv) epicardial fat volume, (xv) cardiac function (ejection fraction), (xvi) stress echocardiogram test results, (xvii) characteristics of the aortic geometry (e.g., cross-sectional area profile along the ascending and descending aorta, and Surface area and volume of the aorta, (xviii) a SYNTAX score, as described above, (xix) plaque burden of existing plaque, (xx) adverse plaque characteristics of existing plaque (e.g., presence of positive remodeling, presence of low attenuation plaque, presence of spotty calcification), (xxi) characteristics of the coronary branch geometry, (xxii) characteristics of coronary cross-sectional area, (xxiii) characteristics of coronary lumen intensity, e.g., intensity change along the centerline (slope of linearly-fitted intensity variation), (xxiv) characteristics of surface of coronary geometry, e.g., 3D surface curvature of geometry (Gaussian, maximum, minimum, mean), (xxv) characteristics of volume of coronary geometry, e.g., ratio of total coronary volume compared to myocardial volume, (xxvi) characteristics of coronary centerline, (xxvii) characteristics of coronary deformation, (xxviii) characteristics of existing plaque, and/or (xxix) characteristics of coronary hemodynamics derived from computational flow dynamics or invasive measurement.

In one embodiment, the characteristics of the coronary branch geometry may include one or more of: (1) total number of vessel bifurcations, and the number of upstream/downstream vessel bifurcations; (2) average, minimum, and maximum upstream/downstream cross-sectional areas; (3) distances (along the vessel centerline) to the centerline point of minimum and maximum upstream/downstream cross-sectional areas, (4) cross-sectional area of and distance (along the vessel centerline) to the nearest upstream/downstream vessel bifurcation, (5) cross-sectional area of and distance (along the vessel centerline) to the nearest coronary outlet and aortic inlet/outlet, (6) cross-sectional areas and distances (along the vessel centerline) to the downstream coronary outlets with the smallest/largest cross-sectional areas, and/or (7) upstream/downstream volumes of the coronary vessels.

In one embodiment, the characteristics of coronary cross-sectional area may include one or more of: (1) cross-sectional lumen area along the coronary centerline, (2) cross-sectional lumen area to the power of N (where N can be determined from various source of scaling laws such as Murray's law (N=1.5) and Uylings' study (N=1.165~1.5)), (3) a ratio of lumen cross-sectional area with respect to the main ostia (LM, RCA) (e.g., measure of cross-sectional area at the LM ostium, normalized cross-sectional area of the left coronary by LM ostium area, measure of cross-sectional area at the RCA ostium, normalized cross-sectional area of the right coronary by RCA ostium area, (4) ratio of lumen cross-sectional area with respect to the main ostia to the power of N (where power can be determined from various source of scaling laws such as Murray's law (N=1.5) and Uylings' study (N=1.165~1.5)), (5) degree of tapering in cross-sectional lumen area along the centerline (based on a sample centerline points within a certain interval (e.g., twice the diameter of the vessel) and compute a slope of linearly-fitted cross-sectional area), (6) location of stenotic lesions (based on detecting minima of cross-sectional area curve (e.g., detecting locations, where first derivative of area curve is zero and second derivative is positive, and smoothing cross-sectional area profile to avoid detecting artifactual peaks), and computing distance (parametric arc length of centerline) from the main ostium, (7) length of stenotic lesions (computed based on the proximal and distal locations from the stenotic lesion, where cross-sectional area is recovered, (8) degree of stenotic lesions, by evaluating degree of stenosis based on reference values of smoothed cross-sectional area profile using Fourier smoothing or kernel regression, (9) location and number of lesions corresponding to 50%, 75%, 90% area reduction, (10) distance from stenotic lesion to the main ostia, and/or (11) irregularity (or circularity) of cross-sectional lumen boundary.

In one embodiment, the characteristics of coronary centerline may include: (1) curvature (bending) of coronary centerline, such as by computing Frenet curvature, based on $$\kappa = \frac{|p' \times p''|}{|p'|^3},$$

where ρ is a coordinate of the centerline, and computing an inverse of the radius of a circumscribed circle along the centerline points, and/or (2) tortuosity (non-planarity) of coronary centerline, such as by computing Frenet torsion, based on $$\tau = \frac{(p' \times p'') \cdot p'''}{|p' \times p''|^2},$$

where ρ is a coordinate of the centerline.

In one embodiment, calculation of the characteristics of coronary deformation may involve multi-phase CCTA (e.g., diastole and systole), including (1) distensibility of coronary artery over cardiac cycle, (2) bifurcation angle change over cardiac cycle, and/or (3) curvature change over cardiac cycle. In one embodiment, the characteristics of existing plaque may be calculated based on: (1) volume of plaque, (2) intensity of plaque, (3) type of plaque (calcified, non-calcified), (4) distance from the plaque location to ostium (LM or RCA), and/or (5) distance from the plaque location to the nearest downstream/upstream bifurcation.

In one embodiment, the characteristics of coronary hemodynamics may be derived from computational flow dynamics or invasive measurement. For example, pulsatile flow simulation may be performed to obtain transient characteristics of blood, by using a lumped parameter coronary vascular model for downstream vasculatures, inflow boundary condition with coupling a lumped parameter heart model and a closed loop model to describe the intramyocardial pressure variation resulting from the interactions between the heart and arterial system during cardiac cycle. For example, the calculation may include one or more of: measured FFR, coronary flow reserve, pressure distribution, FFRct, mean wall-shear stress, oscillatory shear index, particle residence time, turbulent kinetic energy, Reynolds number, Womersley number, and/or local flow rate.

Method 500 may then include associating the feature vector with the growth, shrinkage, or onset of plaque at each point of the patient-specific geometric model (step 516). Method 500 may involve continuing to perform the above steps 512, 514, 516, for each of a plurality of points in the patient-specific geometric model (step 518), and for each of any number of patients for which a machine learning algorithm may be based (step 520). Method 500 may also involve continuing to perform the above steps 512, 514, 516, for each of a plurality of points in the patient-specific geometric model, and for each of any number of patients for which a machine learning algorithm may be based, across any additional time period or periods useful for generating information about the growth, shrinkage, or onset of plaque (i.e., the change and/or rate of change of plaque at each point of the model) (step 522).

Method 500 may then include training a machine learning algorithm to predict the probability of amounts of growth, shrinkage, or onset of plaque at the points from the feature vectors at the points (step 524). Examples of machine learning algorithms suitable for performing this task may include support vector machines (SVMs), multi-layer perceptrons (MLPs), and/or multivariate regression (MVR) (e.g., weighted linear or logistic regression). In one embodiment, if training data causes the machine learning algorithm to predict a lower amount (e.g., size or extent) of plaque than what is detected, then the machine learning algorithm may be interpreted as predicting plaque shrinkage; if training data causes the machine learning algorithm to predict a higher amount (e.g., size or extent) of plaque than what is detected, then the machine learning algorithm may be interpreted as predicting plaque growth.

Method 500 may then include storing or otherwise saving the results of the machine learning algorithm (e.g., feature weights) to a digital representation, such as the memory or digital storage (e.g., hard drive, network drive) of a computational device, such as a computer, laptop, DSP, server, etc. of server systems 106 (step 526).

Figure 5B:
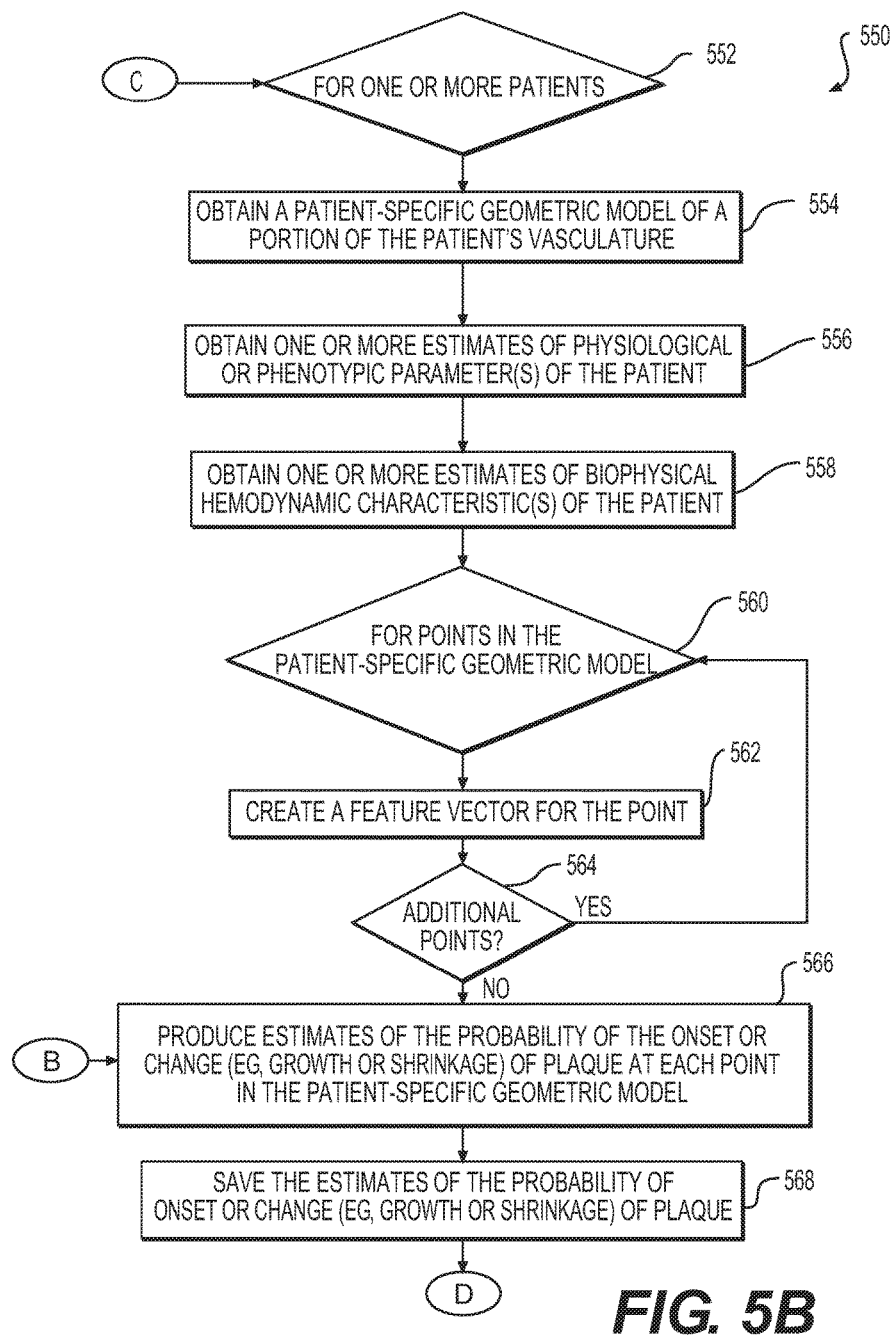
FIG. 5B is a block diagram of an exemplary method of using a trained machine learning system for predicting the onset and/or change (e.g., rate of growth/shrinkage) of coronary lesions from vessel geometry, physiology, and hemodynamics, according to an exemplary embodiment of the present disclosure.

FIG. 5B is a block diagram of an exemplary method of using the machine learning system (e.g., machine learning system 310 executed on server systems 106) for predicting, for a particular patient, the rate of onset, growth/shrinkage, of coronary lesions from vessel geometry, physiology, and hemodynamics, according to an exemplary embodiment of the present disclosure. In one embodiment, method 550 may include, for one or more patients (step 552), obtaining a patient-specific geometric model of a portion of the patient's vasculature (step 554), obtaining one or more estimates of physiological or phenotypic parameters of the patient (step 556), and obtaining one or more estimates of biophysical hemodynamic characteristics of the patient (step 558).

Specifically, the step of obtaining a patient-specific geometric model of a portion of the patient's vasculature (step 554) may include obtaining a patient-specific model of the geometry for one or more of the patient's blood vessels, myocardium, aorta, valves, plaques, and/or chambers. In one embodiment, this geometry may be represented as a list of points in space (possibly with a list of neighbors for each point) in which the space can be mapped to spatial units between points (e.g., millimeters). In one embodiment, this model may be derived by performing a cardiac CT imaging of the patient in the end diastole phase of the cardiac cycle. This image then may be segmented manually or automatically to identify voxels belonging to the aorta and the lumen of the coronary arteries. Inaccuracies in the geometry extracted automatically may be corrected by a human observer who compares the extracted geometry with the images and makes corrections as needed. Once the voxels are identified, the geometric model can be derived (e.g., using marching cubes).

In one embodiment, the step of obtaining one or more estimates of physiological or phenotypic parameters of the patient (step 556) may include obtaining a list of one or more estimates of physiological or phenotypic parameters of the patient, such as blood pressure, blood viscosity, in vitro blood test results (e.g., LDL/Triglyceride cholesterol level), patient age, patient gender, the mass of the supplied tissue, etc. These parameters may be global (e.g., blood pressure) or local (e.g., estimated density of the vessel wall at a location). In one embodiment, the physiological or phenotypic parameters may include, blood pressure, hematocrit level, patient age, patient gender, myocardial mass (e.g., derived by segmenting the myocardium in the image, and calculating the volume in the image and using an estimated density of 1.05 g/mL to estimate the myocardial mass), general risk factors of coronary artery disease (e.g., smoking, diabetes, hypertension, abdominal obesity, dietary habits, family history, etc.), and/or in vitro blood test results (e.g., LDL, Triglyceride cholesterol level).

In one embodiment, the step of obtaining one or more estimates of biophysical hemodynamic characteristics of the patient (step 558) may include obtaining a list of one or more estimates of biophysical hemodynamic characteristics from computational fluid dynamics analysis, such as wall-shear stress, oscillatory shear index, particle residence time, Reynolds number, Womersley number, local flow rate, and turbulent kinetic energy, etc. Specifically, the mean wall-shear stress, may be defined as $$\left| \frac{1}{T_1 - T_0} \int_{T_0}^{T_1} \vec{t}_s \, dt \right| \cdot \vec{t}_s,$$

which may be the wall shear stress vector defined as the in-plane component of the surface traction vector. The oscillatory shear index (OSI), may be defined as $$\frac{1}{2}\left(1 - \frac{\left|\frac{1}{T_1 - T_0} \int_{T_0}^{T_1} \vec{t}_s \, dt\right|}{\frac{1}{T_1 - T_0} \int_{T_0}^{T_1} |\vec{t}_s| \, dt}\right),$$

which may be a measure of the uni-directionality of shear stress. The particle residence time may be a measure of the time it takes blood to be flushed from a specified fluid domain. The turbulent kinetic energy (TKE) may be a measure of the intensity of turbulence associated with eddies in turbulent flow, and may be characterized by measured root-mean-square velocity fluctuation, and may be normalized by kinetic energy. The Reynolds number may be defined as $$\frac{\rho UD}{\mu}$$

where (ρ: density of blood, U: average flow velocity, D: vessel diameter, μ: dynamic viscosity). The Womersley number may be defined as $$\frac{D}{2}\sqrt{\frac{\varpi\rho}{\mu}}$$

where ($\overline{\omega}$: angular frequency, equal to $$\frac{1}{\text{cardiac cycle length}}).$$

Method 550 may include, for every point in the patient-specific geometric model (step 560), creating for that point a feature vector comprising a numerical description of the geometry and biophysical hemodynamic characteristic at that point, and estimates of physiological or phenotypic parameters of the patient. Global physiological or phenotypic parameters can be used in the feature vector of all points and local physiological or phenotypic parameters can change in the feature vector of different points. Method 550 may involve continuing to perform the above steps 560, 562, for each of a plurality of points in the patient-specific geometric model (step 564).

Method 550 may then include producing estimates of the probability and/or rate of the growth, shrinkage, or onset of plaque at each point in the patient-specific geometric model based on the stored machine learning results (stored at B, FIG. 5A) (step 566). Specifically, method 550 may use the saved results of the machine learning algorithm produced in the training mode of method 500 (e.g., feature weights) to produce estimates of the probability of growth, shrinkage, or onset (e.g., rates of growth/shrinkage) of plaque at each point in the patient-specific geometric model (e.g., by generating plaque estimates as a function of the feature vector at each point). These estimates may be produced using the same machine learning algorithm technique used in the training mode (e.g., the SVM, MLP, MVR technique). Method 550 may then include saving the estimates of the probability of the growth, shrinkage, or onset of plaque (step 568), such as to the memory or digital storage (e.g., hard drive, network drive) of a computational device, such as a computer, laptop, DSP, server, etc., of server systems 106, and communicating these patient-specific and location-specific predicted probabilities of lesion formation to a health care provider.

Figure 6:
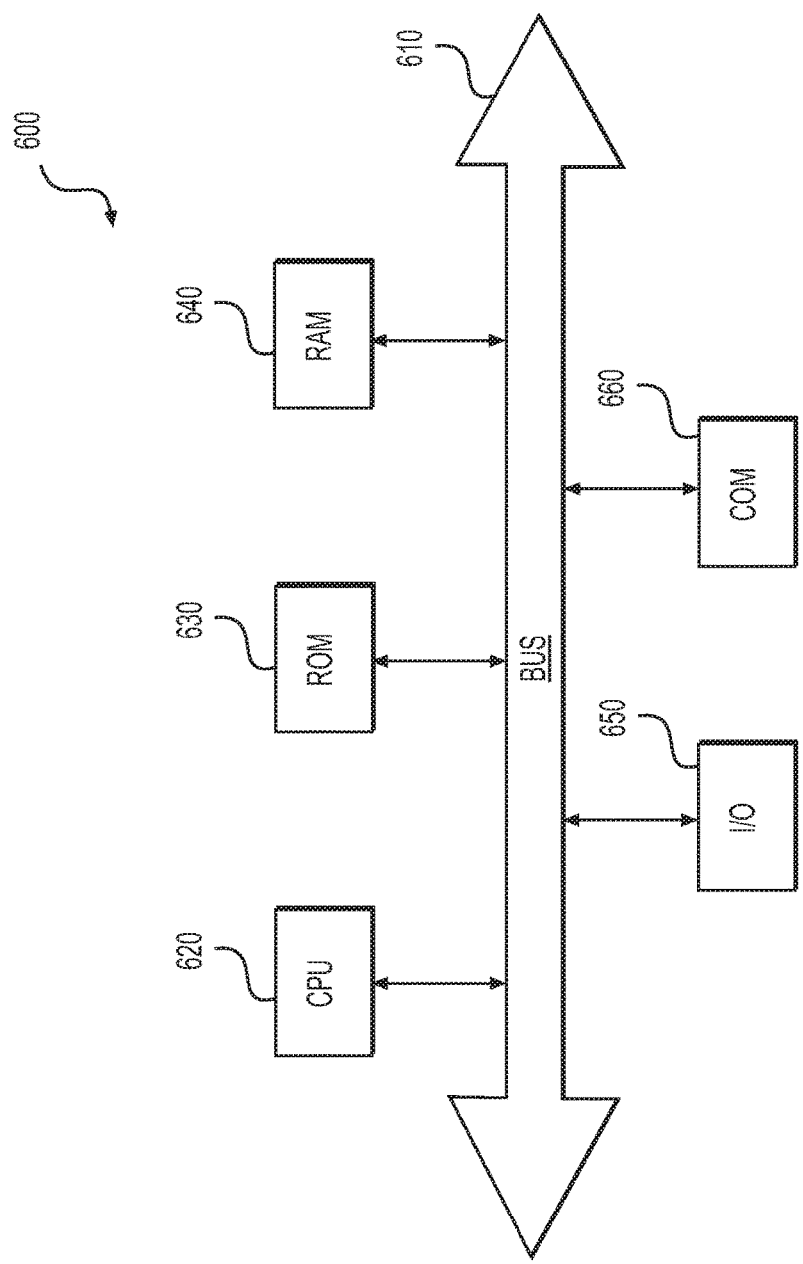
FIG. 6 is a simplified block diagram of an exemplary computer system in which embodiments of the present disclosure may be implemented.

FIG. 6 is a simplified block diagram of an exemplary computer system 600 in which embodiments of the present disclosure may be implemented, for example as any of the physician devices or servers 102, third party devices or servers 104, and server systems 106. A platform for a server 600, for example, may include a data communication interface for packet data communication 660. The platform may also include a central processing unit (CPU) 620, in the form of one or more processors, for executing program instructions. The platform typically includes an internal communication bus 610, program storage and data storage for various data files to be processed and/or communicated by the platform such as ROM 630 and RAM 640, although the server 600 often receives programming and data via a communications network (not shown). The hardware elements, operating systems and programming languages of such equipment are conventional in nature, and it is presumed that those skilled in the art are adequately familiar therewith. The server 600 also may include input and output ports 650 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

As described above, the computer system 600 may include any type or combination of computing systems, such as handheld devices, personal computers, servers, clustered computing machines, and/or cloud computing systems. In one embodiment, the computer system 600 may be an assembly of hardware, including a memory, a central processing unit ("CPU"), and/or optionally a user interface. The memory may include any type of RAM or ROM embodied in a physical storage medium, such as magnetic storage including floppy disk, hard disk, or magnetic tape; semiconductor storage such as solid state disk (SSD) or flash memory; optical disc storage; or magneto-optical disc storage. The CPU may include one or more processors for processing data according to instructions stored in the memory. The functions of the processor may be provided by a single dedicated processor or by a plurality of processors. Moreover, the processor may include, without limitation, digital signal processor (DSP) hardware, or any other hardware capable of executing software. The user interface may include any type or combination of input/output devices, such as a display monitor, touchpad, touchscreen, microphone, camera, keyboard, and/or mouse.

Program aspects of the technology may be thought of as "products" or "articles of manufacture" typically in the form of executable code and/or associated data that is carried on or embodied in a type of machine readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links or the like, also may be considered as media bearing the software. As used herein, unless restricted to non-transitory, tangible "storage" media, terms, such as computer or machine "readable medium" refer to any medium that participates in providing instructions to a processor for execution.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for image processing, the system comprising:
a data storage device storing instructions for image processing; and
a processor configured to execute the instructions to perform a method comprising:
receiving time-varying images of a blood vessel with known plaque information at one or more points of the blood vessel;
receiving physiological and hemodynamic information at one or more points of the blood vessel for each of the received time-varying images with known plaque information;
determining changes in anatomical data over time at one or more points of the blood vessel for the received time-varying images;
creating feature vectors comprising: (1) features of the received physiological and hemodynamic information and (2) features of the determined changes in anatomical data, which are predictive of the plaque information of the blood vessel, at one or more points of the blood vessel for each of the received time-varying images with known plaque information;
associating the feature vectors with the plaque information at one or more points of the blood vessel for each of the received time-varying images;
training a machine learning algorithm for predicting plaque information from a patient at one or more points of a blood vessel, using the associated feature vectors;
receiving time-varying images of a blood vessel of a patient with unknown plaque information related to vascular hemodynamics of the blood vessel;
receiving physiological and hemodynamic information of the blood vessel of the patient for each of the received time-varying images with unknown plaque information;
determining changes in anatomical data over time for the received time-varying images of the blood vessel of the patient with unknown plaque information;
creating feature vectors comprising: (1) features of the received physiological and hemodynamic information and (2) features of the determined changes in anatomical data, which are predictive of the plaque information of the blood vessel, at one or more points of the blood vessel for each of the received time-varying images with unknown plaque information of the patient;
determining plaque information of the blood vessel of the patient, by inputting the created feature vectors for each of the received time-varying images with unknown plaque information of the patient into the trained machine learning algorithm; and
generating, using a computer processor, a patient-specific prediction or a patient-specific probability of a development of artery disease for the patient, using the determined plaque information.

2. The system according to claim 1, wherein the processor is further configured for identifying a target region of the received time-varying images of the blood vessel of the patient to determine functional information.

3. The system according to claim 2, wherein the processor is configured for: identifying the plaque information of the blood vessel of the patient by generating a geometric model; and
performing a blood flow simulation using computational flow dynamics.

4. The system according to claim 2, wherein the processor is configured for:
determining changes in anatomical data over time with respect to the identified target region in the blood vessel region, on a basis of the received time-varying images;
generating a geometric model related to the identified target region, on the basis of the received time-varying images and the determined changes in anatomical data over time; and
analyzing the geometric model to determine (1) features of the received physiological and hemodynamic information and (2) features of the determined changes in anatomical data, which are predictive of the plaque information of the blood vessel, at one or more points of the blood vessel.

5. The system according to claim 1, wherein the physiological and hemodynamic characteristics includes at least one of a cross-sectional area of the blood vessel.

6. The system according to claim 1, wherein the processor is further configured for: mapping features of training data, which includes (1) the received physiological and hemodynamic information and (2) the determined changes in anatomical data that are predictive of the plaque information of the blood vessel, with the known plaque information at one or more points of the blood vessel.

7. The system according to claim 1, wherein the processor is configured for: identifying plaque information of the blood vessel of the patient by further using a change in intensity value of the received time-varying images.

8. The system according to claim 1, wherein the features of the received physiological and hemodynamic information and the determined changes in anatomical data that are predictive of the functional information includes features that are determined by a lumped parameter model.

9. The system according to claim 1, wherein the change in anatomical data includes a change in blood vessel cross-sectional area and a change amount in the radius of the blood vessels.

10. The system according to claim 1, wherein the processor is further configured for:
displaying information indicating the plaque information of the blood vessel of the patient;
calculating a change in cross-sectional area of the blood vessel of the patient, as the blood vessel morphology; and
displaying the change in cross-sectional area.

11. The system according to claim 10, wherein the processor is configured for: displaying information indicating an electrocardiographic waveform of the patient during an image taking process and displaying the information indicating the change in anatomical data.

12. The system according to claim 11, wherein the processor is configured for: displaying the information indicating the electrocardiographic waveform so as to be kept in correspondence with the information indicating the change in anatomical data.

13. The system according to claim 10, wherein the processor is configured for: determining a local flow rate of blood flowing through the blood vessel of the patient.

14. The system according to claim 10, wherein the processor is configured for: displaying a geometric model of the blood vessels of the patient and displaying the plaque information.

15. The method of claim 1, wherein the plaque information comprises one or more of: a plaque location, onset, and/or change; an indication of a severity of a plaque; or an indication of an absence or presence of a plaque.

16. An image processing method comprising:
receiving time-varying images of a blood vessel with known plaque information at one or more points of the blood vessel related to vascular hemodynamics;
receiving physiological and hemodynamic information at one or more points of the blood vessel for each of the received time-varying images with known plaque information;
determining changes in anatomical data over time at one or more points of the blood vessel for the received time-varying images with known plaque information;
creating feature vectors comprising: (1) features of the received physiological and hemodynamic information and (2) features of the determined changes in anatomical data, which are predictive of the plaque information of the blood vessel, at one or more points of the blood vessel for each of the received time-varying images with known plaque information;
associating the feature vectors with the plaque information at one or more points of the blood vessel for each of the received time-varying images;
training a machine learning algorithm for predicting plaque information from a patient at one or more points of a blood vessel, using the associated feature vectors;
receiving time-varying images of a blood vessel of a patient with unknown plaque information related to vascular hemodynamics of the blood vessel;
receiving physiological and hemodynamic information of the blood vessel of the patient for each of the received time-varying images with unknown plaque information;
determining changes in anatomical data over time for the received time-varying images of the blood vessel of the patient with unknown plaque information;
creating feature vectors comprising: (1) features of the received physiological and hemodynamic information and (2) features of the determined changes in anatomical data, which are predictive of the plaque information of the blood vessel, at one or more points of the blood vessel for each of the received time-varying images with unknown plaque information of the patient;
determining plaque information of the blood vessel of the patient, by inputting the created feature vectors for each of the received time-varying images with unknown plaque information of the patient into the trained machine learning algorithm; and
generating, using a computer processor, a patient-specific prediction or a patient-specific probability of a development of artery disease for the patient, using the determined plaque information.

17. A non-transitory computer-readable storage medium having recorded thereon a plurality of computer-executable instructions that cause the computer to execute:
receiving time-varying images of a blood vessel with known plaque information at one or more points of the blood vessel related to vascular hemodynamics;
receiving physiological and hemodynamic information at one or more points of the blood vessel for each of the received time-varying images with known plaque information;
determining changes in anatomical data over time at one or more points of the blood vessel for the received time-varying images with known plaque information;
creating feature vectors comprising: (1) features of the received physiological and hemodynamic information and (2) features of the determined changes in anatomical data, which are predictive of the plaque information of the blood vessel, at one or more points of the blood vessel for each of the received time-varying images with known plaque information;
associating the feature vectors with the plaque information at one or more points of the blood vessel for each of the received time-varying images;
training a machine learning algorithm for predicting plaque information from a patient at one or more points of a blood vessel, using the associated feature vectors;
receiving time-varying images of a blood vessel of a patient with unknown plaque information related to vascular hemodynamics of the blood vessel;
receiving physiological and hemodynamic information of the blood vessel of the patient for each of the received time-varying images with unknown plaque information;
determining changes in anatomical data over time for the received time-varying images of the blood vessel of the patient with unknown plaque information;
creating feature vectors comprising: (1) features of the received physiological and hemodynamic information and (2) features of the determined changes in anatomical data, which are predictive of the plaque information of the blood vessel, at one or more points of the blood vessel for each of the received time-varying images with unknown plaque information of the patient;
determining plaque information of the blood vessel of the patient, by inputting the created feature vectors for each of the received time-varying images with unknown plaque information of the patient into the trained machine learning algorithm; and
generating, using a computer processor, a patient-specific prediction or a patient-specific probability of a development of artery disease for the patient, using the determined plaque information.

* * * * *